(12) United States Patent
Nishigishi

(10) Patent No.: US 10,357,276 B2
(45) Date of Patent: Jul. 23, 2019

(54) MEDICAL DEVICE

(71) Applicant: ASAHI INTECC CO., LTD., Nagoya-shi, Aichi (JP)

(72) Inventor: Makoto Nishigishi, Owariasahi (JP)

(73) Assignee: ASAHI INTECC CO., LTD., Seto-shi (JP)

( * ) Notice: Subject to any disclaimer, the term of this patent is extended or adjusted under 35 U.S.C. 154(b) by 34 days.

(21) Appl. No.: 15/393,967

(22) Filed: Dec. 29, 2016

(65) Prior Publication Data

US 2017/0319231 A1    Nov. 9, 2017

(30) Foreign Application Priority Data

May 9, 2016    (JP) .................................. 2016-094143

(51) Int. Cl.
*A61B 17/3207*    (2006.01)
*A61M 25/10*    (2013.01)
(Continued)

(52) U.S. Cl.
CPC ... *A61B 17/320725* (2013.01); *A61M 25/104* (2013.01); *A61B 17/221* (2013.01); *A61B 2017/00477* (2013.01); *A61B 2017/00544* (2013.01); *A61B 2017/00778* (2013.01); *A61B 2017/00818* (2013.01); *A61B 2017/22061* (2013.01); *A61M 2025/109* (2013.01)

(58) Field of Classification Search
CPC ....... A61B 17/320725; A61B 17/3207; A61M 2025/109; A61M 25/104
See application file for complete search history.

(56) References Cited

U.S. PATENT DOCUMENTS 5,196,024 A    3/1993 Barath
5,797,935 A *  8/1998 Barath ........... A61B 17/320725
                                              606/159
(Continued)

FOREIGN PATENT DOCUMENTS

JP    2015-173913 A    10/2015
WO    2009/116159 A1    9/2009
WO    2013/023121 A1    2/2013

OTHER PUBLICATIONS

Jul. 5, 2017 Extended European Search Report issued in European Patent Application No. 16203575.2.
(Continued)

*Primary Examiner* — Sarah A Simpson
(74) *Attorney, Agent, or Firm* — Oliff PLC

(57) ABSTRACT

A medical device includes an expandable-and-contractible member capable of radially expanding and radially contracting, an incising member disposed on an outer circumference of the expandable-and-contractible member and having a hollow portion, a core wire inserted in the hollow portion, a distal tip, and a ring. The core wire is capable of sliding in a longitudinal direction of the medical device as the expandable-and-contractible member expands or contracts. The incising member is therefore not likely to come off upon radial expansion or radial contraction of the expandable-and-contractible member, and is therefore not likely to interfere with the expanding or contracting movement of the expandable-and-contractible member.

10 Claims, 16 Drawing Sheets

(51) Int. Cl.
    *A61B 17/00*            (2006.01)
    *A61B 17/221*         (2006.01)
    *A61B 17/22*           (2006.01)

(56) References Cited

U.S. PATENT DOCUMENTS

| | | |
|---|---|---|
| 8,123,770 B2 | 2/2012 | Olsen et al. |
| 2008/0228139 A1 | 9/2008 | Melsheimer et al. |
| 2009/0171284 A1 | 7/2009 | Burke et al. |
| 2011/0264128 A1* | 10/2011 | Mauch ........... A61B 17/320725 606/170 |
| 2012/0022563 A1* | 1/2012 | Leffel ................ A61M 25/104 606/159 |
| 2013/0041391 A1 | 2/2013 | Spencer et al. |

OTHER PUBLICATIONS

Jan. 8, 2019 Office Action issued in Korean Patent Application No. 10-2016-0172501.

* cited by examiner

MEDICAL DEVICE

CROSS REFERENCE TO RELATED APPLICATION

This application claims priority to Japanese Application No. 2016-094143 filed on May 9, 2016, the contents of which are incorporated by reference herein in their entirety.

BACKGROUND

The disclosed embodiments relate to a medical device comprising an incising member for incising a stenosis or stricture in a blood vessel or in a digestive organ in a longitudinal direction of the blood vessel or digestive organ.

Conventionally, a stenosis or stricture formed in a blood vessel or in a digestive organ is treated by a well-known method, in which the stenosis or stricture is dilated with a medical device such as a balloon catheter. Such a medical device generally has an expandable-and-contractible member capable of radially expanding and radially contracting (a balloon or a mesh member, for example), and the expandable-and-contractible member radially expands to dilate the stenosis or stricture.

When the stenosis or stricture is highly calcified, however, it is difficult to dilate it with the expandable-and-contractible member alone. So, in this situation, a known medical device (an incising device) is used that has an incising member disposed in the longitudinal direction of the medical device. To operate the medical device, a balloon catheter is inserted into the interior of the incising member and then the balloon is expanded so as to radially expand the incising member (see U.S. Patent Application Publication No. 2013/0041391 discussed below, for example).

In the medical device of U.S. Patent Application Publication No. 2013/0041391, the incising member (a cutting element), which is disposed in the longitudinal direction, is directly fixed to an outer circumference of the expandable-and-contractible member (an expandable scaffold). That is, the incising member is directly fixed to a wire that constitutes the expandable-and-contractible member. Upon radial expansion, the expandable-and-contractible member can incise a stenosis or stricture in the longitudinal direction.

Generally, as the expandable-and-contractible member expands radially, it contracts in the longitudinal direction (in other words, as the expandable-and-contractible member expands, it becomes shorter). In the medical device described above, the incising member is directly fixed to the outer circumference of the expandable-and-contractible member via the wire that constitutes the expandable-and-contractible member and therefore cannot move in the longitudinal direction as the expandable-and-contractible member expands or contracts. Consequently, upon attempted radial expansion of the balloon of the balloon catheter inserted in the interior of the expandable-and-contractible member, the radial expansion of the expandable-and-contractible member is interfered with by the incising member, which is a problem. In addition, when the expandable-and-contractible member is forced to expand, the incising member comes off the expandable-and-contractible member, which is another problem.

Sometimes, upon expansion of the expandable-and-contractible member, the stenosis or stricture can be partially caught between the expandable-and-contractible member and the incising member. When the handler manipulates the medical device in the longitudinal direction, the stenosis or stricture thus caught can cause the incising member to come off the expandable-and-contractible member, which is another problem.

SUMMARY

The disclosed embodiments are devised based on the above circumstances, and an object of the disclosed embodiments is to provide a medical device in which an incising member is not likely to come off upon radial expansion or radial contraction of an expandable-and-contractible member, and in which the incising member is not likely to interfere with the expanding or contracting movement of the expandable-and-contractible member.

This object is achieved in the following ways.

A medical device of the disclosed embodiments comprises an expandable-and-contractible member capable of radially expanding and radially contracting; an incising member disposed on an outer circumference of the expandable-and-contractible member and comprising a hollow portion open toward a proximal end of the medical device; a core wire inserted in the hollow portion of the incising member from the proximal end of the medical device; a distal tip fixed to both a distal end of the expandable-and-contractible member and a distal end of the incising member; and a ring fixed to both a proximal end of the expandable-and-contractible member and a proximal end of the core wire. The core wire is capable of sliding in a longitudinal direction of the medical device within the hollow portion as the expandable-and-contractible member expands or contracts.

Alternatively, the hollow portion may open toward a distal end of the medical device. In this case, the core wire is inserted in the hollow portion of the incising member from the distal end of the medical device; the distal tip is fixed to a distal end of the core wire instead of the distal end of the incising member; and the ring is fixed to a proximal end of the incising member instead of the proximal end of the core wire.

In either configuration, as the expandable-and-contractible member radially expands, part of the core wire housed within the hollow portion of the incising member becomes shorter in the longitudinal direction, while, as the expandable-and-contractible member radially contracts, the part of the core wire housed within the hollow portion of the incising member becomes longer in the longitudinal direction. Because the core wire is housed within in the hollow portion, the incising member does not come off the expandable-and-contractible member as the expandable-and-contractible member expands or contracts and can slide to an optimum position. As a result, the incising member is less likely to interfere with the radial expansion or the radial contraction of the expandable-and-contractible member. Even when the handler manipulates the medical device in the longitudinal direction in a state where the stenosis or stricture is partially caught between the expandable-and-contractible member and the incising member, the core wire can be pulled out of the hollow portion of the incising member (in other words, the core wire and the incising member can become separated from each other), so that the load (external force) applied on the incising member by the stenosis or stricture thus caught can be reduced. This in turn reduces the possibility of the incising member coming off the expandable-and-contractible member.

The expandable-and-contractible member may be a mesh member woven from a first wire and a second wire. Additionally, the core wire may extend in the longitudinal direction underneath a space that is defined by the first wire and the second wire. Because of this configuration, even if the core wire is pulled out of the hollow portion of the incising member (in other words, the core wire and the incising member become separated from each other), the likelihood of the core wire moving outwardly and coming off the mesh member can be reduced. As a result, the possibility of a wall of a normal blood vessel or a wall of a normal digestive organ becoming impaired by the core wire being pulled out of (or separated from) the incising member can be reduced.

DETAILED DESCRIPTION OF EMBODIMENTS

Figure 1:
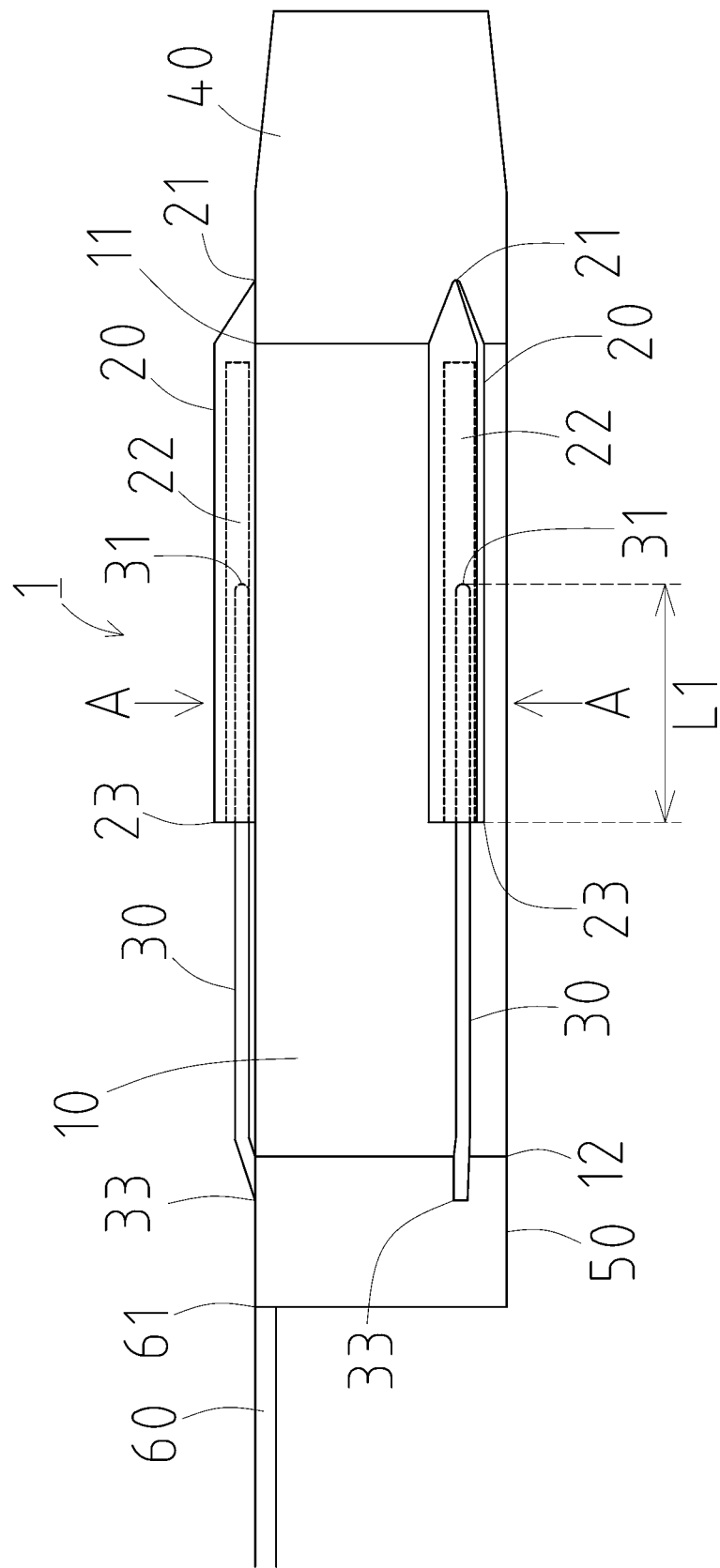
FIG. 1 is an overall view of a medical device according to the disclosed embodiments, in which an expandable-and-contractible member is radially contracted.
Figure 2:
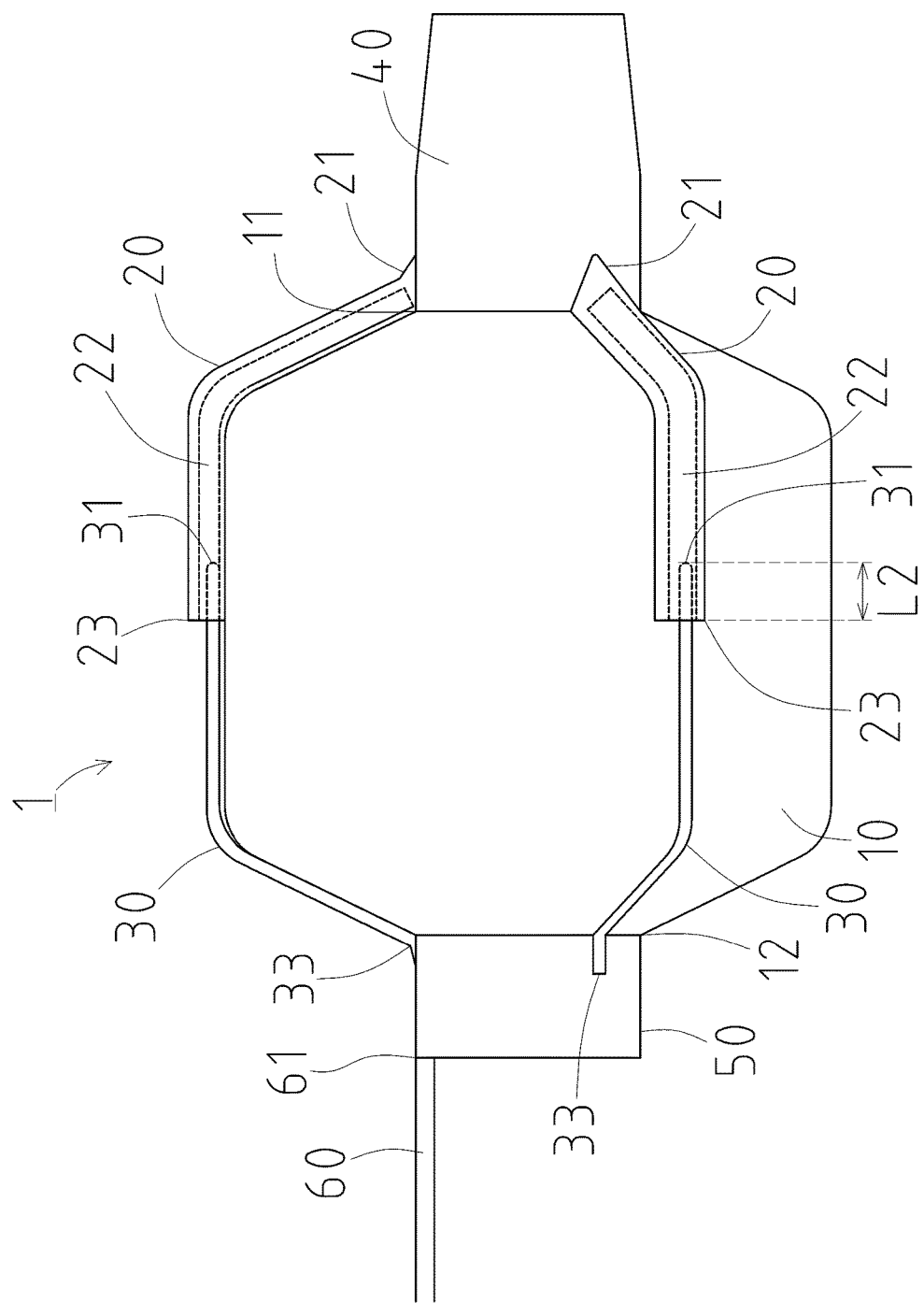
FIG. 2 is an overall view of the medical device shown in FIG. 1, in which the expandable-and-contractible member is radially expanded.

A medical device 1 according to the disclosed embodiments is described below referring to FIG. 1 to FIG. 3. In FIGS. 1 and 2, as well as in FIGS. 4-7 and 9-15, the distal end (the front end) to be inserted into the body is shown to the right-hand side, and the proximal end (the read end, also called the base end) to be manipulated by a handler such as a doctor is shown to the left-hand side. FIG. 1 shows an expandable-and-contractible member 10 radially contracted, and FIG. 2 shows the expandable-and-contractible member 10 radially expanded.

The medical device 1 is, for example, a therapeutic device used for dilating a stenosis or stricture for curative purposes. As shown in FIG. 1 and FIG. 2, the medical device 1 comprises the expandable-and-contractible member 10 capable of radially expanding and radially contracting, at least one incising member 20, at least one core wire 30, a distal tip 40, a ring 50, and a shaft 60.

The expandable-and-contractible member 10 may be made of a resin material and is capable of radially expanding and radially contracting. A distal end 11 of the expandable-and-contractible member 10 is fixed to the distal tip 40, and a proximal end 12 of the expandable-and-contractible member 10 is fixed to the ring 50.

The at least one incising member 20 is disposed in the longitudinal direction of the medical device 1 on an outer circumference of the expandable-and-contractible member 10 and comprises a hollow portion 22 that is open toward a proximal end of the medical device. A distal end 21 of the incising member 20 is fixed to the distal tip 40, and a proximal end 23 of the incising member 20 is not fixed to the expandable-and-contractible member 10 and remains unconstrained. In other words, the incising member 20 is not fixed to the expandable-and-contractible member 10 except for its distal end 21 being fixed to the distal tip 40. The medical device 1 shown in FIG. 3 includes three incising members 20.

The at least one core wire 30 is disposed in the longitudinal direction on the outer circumference of the expandable-and-contractible member 10, with a distal end 31 thereof being within the hollow portion 22 of the incising member 20. As to be described below, the distal end 31 of the core wire 30 is not fixed within the hollow portion 22 of the incising member 20 and can slide in the longitudinal direction within the hollow portion 22 of the incising member 20 as the expandable-and-contractible member 10 expands or contracts. A proximal end 33 of the core wire 30 is fixed to the ring 50. The medical device 1 shown in FIG. 3 includes three core wires 30.

The distal tip 40 is fixed to the distal end 11 of the expandable-and-contractible member 10 and the distal end 21 of the incising member 20, and may be made of a resin material.

The ring 50 is fixed to the proximal end 12 of the expandable-and-contractible member 10 and the proximal end 33 of the core wire 30, and may be made of a metal material.

A distal end 61 of the shaft 60 is fixed to the ring 50. The shaft 60 is a thin, cylinder-like metal (e.g., stainless steel) wire extending from the ring 50 in the longitudinal direction toward a proximal end of the medical device 1.

The handler inserts the medical device 1 into a blood vessel or a digestive organ and manipulates the shaft 60 in the longitudinal direction to deliver the medical device 1 to the site of a stenosis or stricture. During this procedure, the expandable-and-contractible member 10 is radially contracted (see FIG. 1). Subsequently, the handler inserts a balloon catheter into the interior of the expandable-and-contractible member 10 of the medical device 1 and then rapidly expands the balloon of the balloon catheter so as to radially expand the expandable-and-contractible member 10 (see FIG. 2). By pressing the incising member 20 against the stenosis or stricture, the handler can incise the stenosis or stricture in the longitudinal direction.

In FIG. 2, the balloon catheter inserted in the interior of the expandable-and-contractible member 10 is omitted for ease of understanding. The balloon catheter used in the medical device 1 can be a known balloon catheter.

Figure 3:
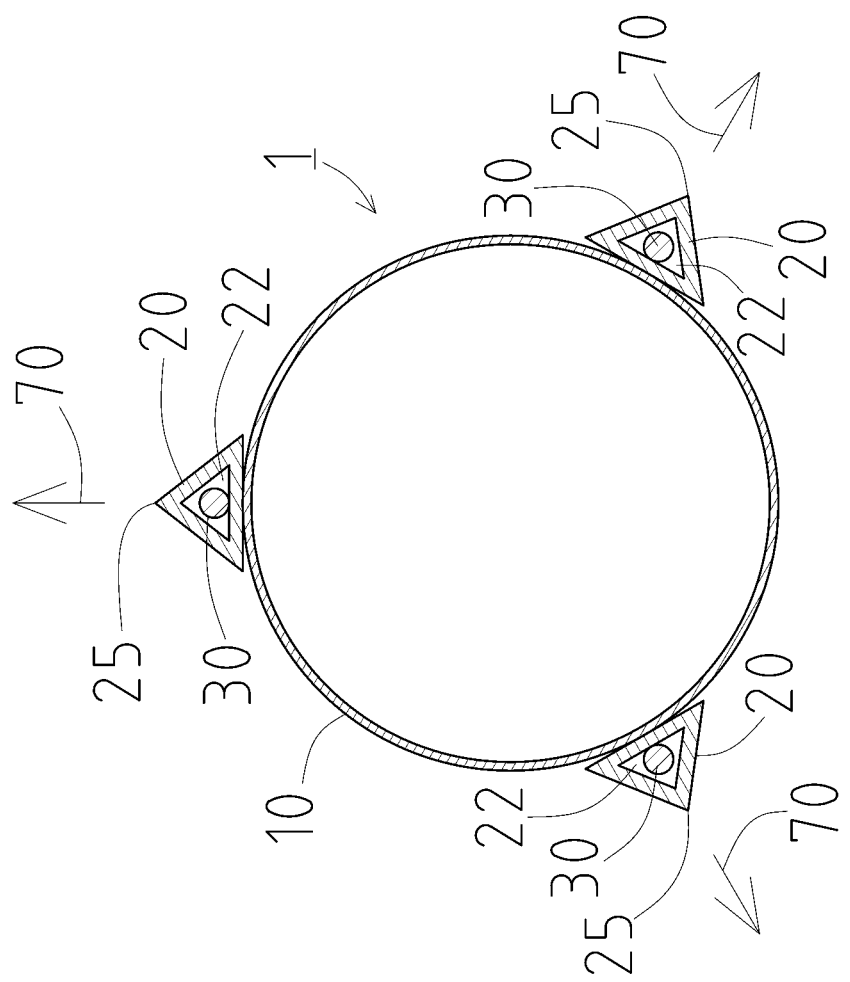
FIG. 3 is a sectional view taken from line A-A of FIG. 1.

FIG. 3 is a sectional view taken from line A-A of FIG. 1. On the outer circumference of the expandable-and-contractible member 10, three incising members 20 are evenly spaced from each other in the circumferential direction (that is, they are spaced 120 degrees from each other in the circumferential direction). The incising member 20 is a triangular tube with its interior being the hollow portion 22, and comprises a protruding portion 25 (one of the corners of the triangle) protruding outwardly. Upon radial expansion of the expandable-and-contractible member 10, the incising member 20 moves in the direction shown by arrow 70, so that the protruding portion 25 of the incising member 20 can incise a stenosis or stricture.

In the medical device 1, the core wire 30, which is inserted in the hollow portion 22 of the incising member 20 from the proximal end of the medical device 1, can slide in the longitudinal direction within the hollow portion 22 as the expandable-and-contractible member 10 expands or contracts. More specifically, upon radial expansion of the expandable-and-contractible member 10 (in other words, upon transitioning from the state shown in FIG. 1 to the state shown in FIG. 2), part of the core wire 30 housed within the hollow portion 22 of the incising member 20 becomes shorter in the longitudinal direction from L1 to L2. That is, less of the core wire 30 is housed within the hollow portion 22 of the incising member 20. Upon radial contraction of the expandable-and-contractible member 10 (in other words, upon transitioning from the state shown in FIG. 2 to the state shown in FIG. 1), the part of the core wire 30 housed within the hollow portion 22 of the incising member 20 becomes longer in the longitudinal direction from L2 to L1 (more of the core wire 30 is housed within the hollow portion 22 of the incising member 20).

As described above, in the medical device 1, the incising member 20 is not fixed to the expandable-and-contractible member 10, and, because the core wire 30 is inserted in the hollow portion 22, the incising member 20 does not come off the expandable-and-contractible member 10 as the expandable-and-contractible member 10 expands or contracts and can slide to an optimum position, consequently reducing the possibility of the incising member 20 interfering with the radial expansion or the radial contraction of the expandable-and-contractible member 10. Even when the stenosis or stricture is partially caught between the expandable-and-contractible member 10 and the incising member 20 and the handler manipulates the medical device 1 in the longitudinal direction in that state, the core wire 30 can be pulled out of the hollow portion 22 of the incising member 20 (in other words, the core wire 30 and the incising member 20 can become separated from each other), so that the load (external force) applied on the incising member 20 by the stenosis or stricture thus caught can be reduced, consequently reducing the possibility of the incising member 20 coming off the expandable-and-contractible member 10.

Figure 4:
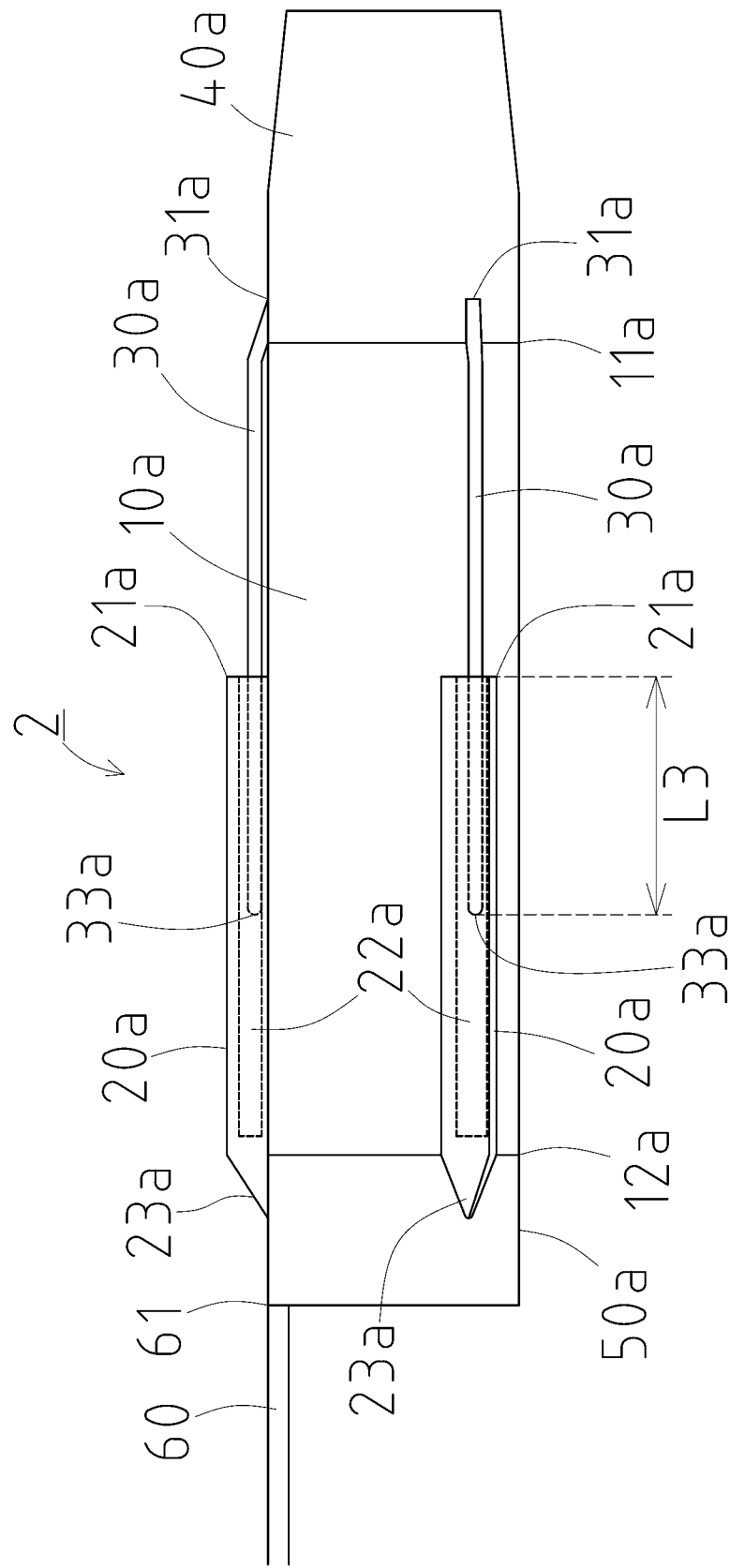
FIG. 4 is an overall view of a medical device according to the disclosed embodiments, in which an expandable-and-contractible member is radially contracted.
Figure 5:
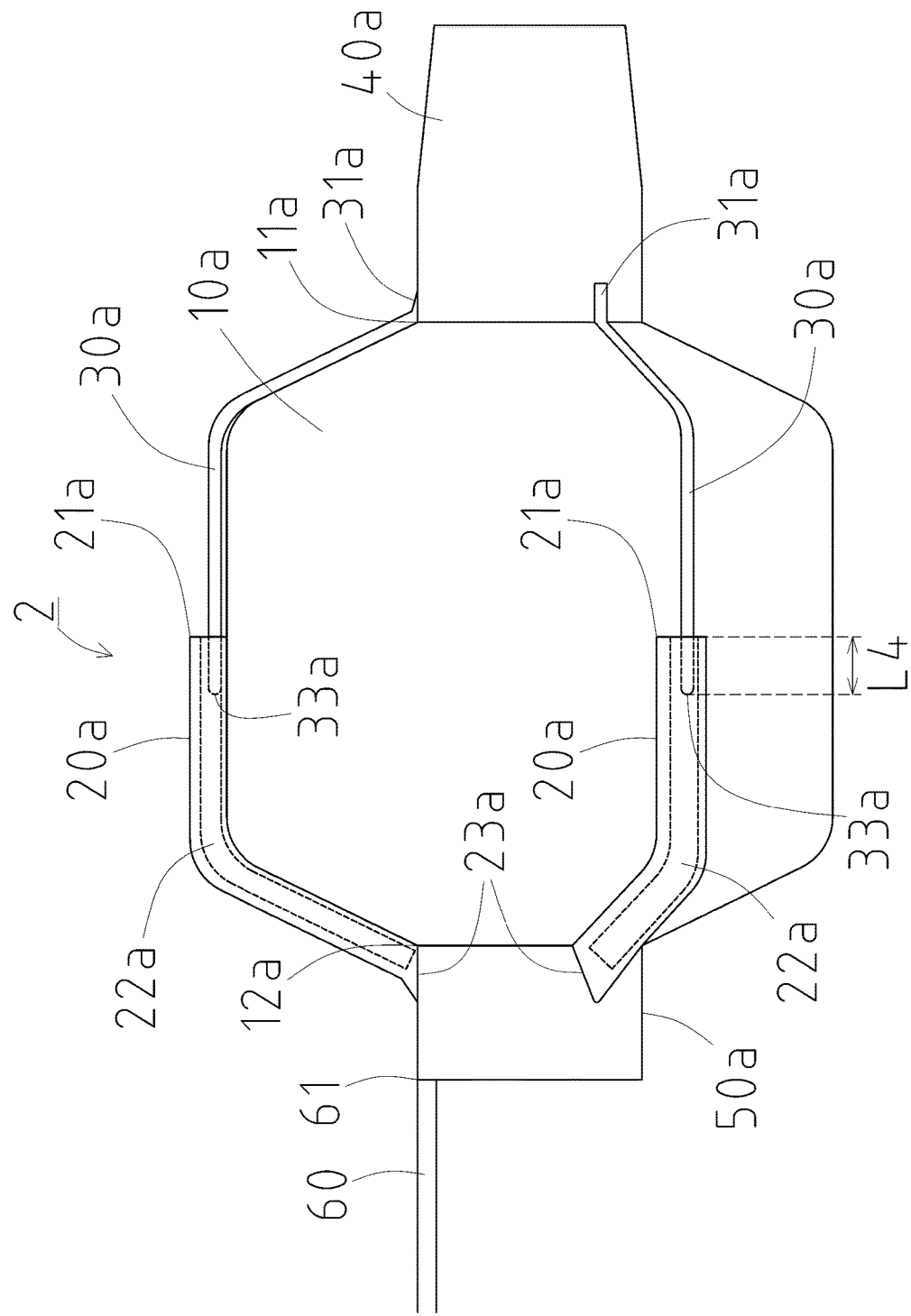
FIG. 5 is an overall view of the medical device shown in FIG. 4, in which the expandable-and-contractible member is radially expanded.

Next, a medical device 2 according to the disclosed embodiments is described below referring to FIG. 4 and FIG. 5. FIG. 4 shows an expandable-and-contractible member 10a radially contracted, and FIG. 5 shows the expandable-and-contractible member 10a radially expanded.

Similarly to the medical device 1, the medical device 2 comprises the expandable-and-contractible member 10a capable of radially expanding and radially contracting, at least one incising member 20a, at least one core wire 30a, a distal tip 40a, a ring 50a, and a shaft 60.

The expandable-and-contractible member 10a may be made of a resin material and is capable of radially expanding and radially contracting. A distal end 11a of the expandable-and-contractible member 10a is fixed to the distal tip 40a, and a proximal end 12a of the expandable-and-contractible member 10a is fixed to the ring 50a.

The at least one incising member 20a is disposed in the longitudinal direction on an outer circumference of the expandable-and-contractible member 10a and comprises a hollow portion 22a that is open toward a distal end of the medical device 2. A distal end 21a of the incising member 20a is not fixed to the expandable-and-contractible member 10a and remains unconstrained, and a proximal end 23a of the incising member 20a is fixed to the ring 50a. In other words, the incising member 20a is not fixed to the expandable-and-contractible member 10a except for its proximal end 23a being fixed to the ring 50a. The medical device 2 includes three incising members 20a on the outer circumference of the expandable-and-contractible member 10a.

The at least one core wire 30a is disposed in the longitudinal direction on the outer circumference of the expandable-and-contractible member 10a, with a proximal end 33a thereof being within the hollow portion 22a of the incising member 20a. As to be described below, the proximal end 33a of the core wire 30a is not fixed within the hollow portion 22a of the incising member 20a and can slide in the longitudinal direction within the hollow portion 22a of the incising member 20a as the expandable-and-contractible member 10a expands or contracts. A distal end 31a of the core wire 30a is fixed to the distal tip 40a.

The distal tip 40a is fixed to the distal end 11a of the expandable-and-contractible member 10a and the distal end 31a of the core wire 30a, and may be made of a resin material.

The ring 50a is fixed to the proximal end 12a of the expandable-and-contractible member 10a and the proximal end 23a of the incising member 20a, and may be made of a metal material.

A distal end 61 of the shaft 60 is fixed to the ring 50a. The shaft 60 is a thin, cylinder-like metal (e.g., stainless steel) wire extending from the ring 50a in the longitudinal direction toward a proximal end of the medical device 2.

The handler inserts the medical device 2 into a blood vessel or a digestive organ and manipulates the shaft 60 in the longitudinal direction to deliver the medical device 2 to the site of a stenosis or stricture. During this procedure, the expandable-and-contractible member 10a is radially contracted (see FIG. 4). Subsequently, the handler inserts a balloon catheter into the interior of the expandable-and-contractible member 10a of the medical device 2 and then rapidly expands the balloon of the balloon catheter so as to radially expand the expandable-and-contractible member 10a (see FIG. 5). By pressing the incising member 20a against the stenosis or stricture, the handler can incise the stenosis or stricture in the longitudinal direction.

In FIG. 5, the balloon catheter inserted in the interior of the expandable-and-contractible member 10a is omitted for ease of understanding. The balloon catheter used in the medical device 2 can be a known balloon catheter.

In the medical device 2, the core wire 30a, which is inserted in the hollow portion 22a of the incising member 20a from the distal end of the medical device 2, can slide in the longitudinal direction within the hollow portion 22a as the expandable-and-contractible member 10a expands or contracts. More specifically, upon radial expansion of the expandable-and-contractible member 10a (in other words, upon transitioning from the state shown in FIG. 4 to the state shown in FIG. 5), part of the core wire 30a housed within the hollow portion 22a of the incising member 20a becomes shorter in the longitudinal direction from L3 to L4. Upon radial contraction of the expandable-and-contractible member 10a (in other words, upon transitioning from the state shown in FIG. 5 to the state shown in FIG. 4), the part of the core wire 30a housed within the hollow portion 22a of the incising member 20a becomes longer in the longitudinal direction from L4 to L3.

As described above, in the medical device 2, the incising member 20a is not fixed to the expandable-and-contractible member 10a, and, because the core wire 30a is inserted in the hollow portion 22a, the incising member 20a does not come off the expandable-and-contractible member 10a as the expandable-and-contractible member 10a expands or contracts and can slide to an optimum position, consequently reducing the possibility of the incising member 20a interfering with the radial expansion or the radial contraction of the expandable-and-contractible member 10a. Even when the stenosis or stricture is partially caught between the expandable-and-contractible member 10a and the incising member 20a and the handler manipulates the medical device 2 in the longitudinal direction in that state, the core wire 30a can be pulled out of the hollow portion 22a of the incising member 20a (in other words, the core wire 30a and the incising member 20a can become separated from each other), so that the load (external force) applied on the incising member 20a by the stenosis or stricture thus caught can be reduced, consequently reducing the possibility of the incising member 20a coming off the expandable-and-contractible member 10a.

Figure 6:
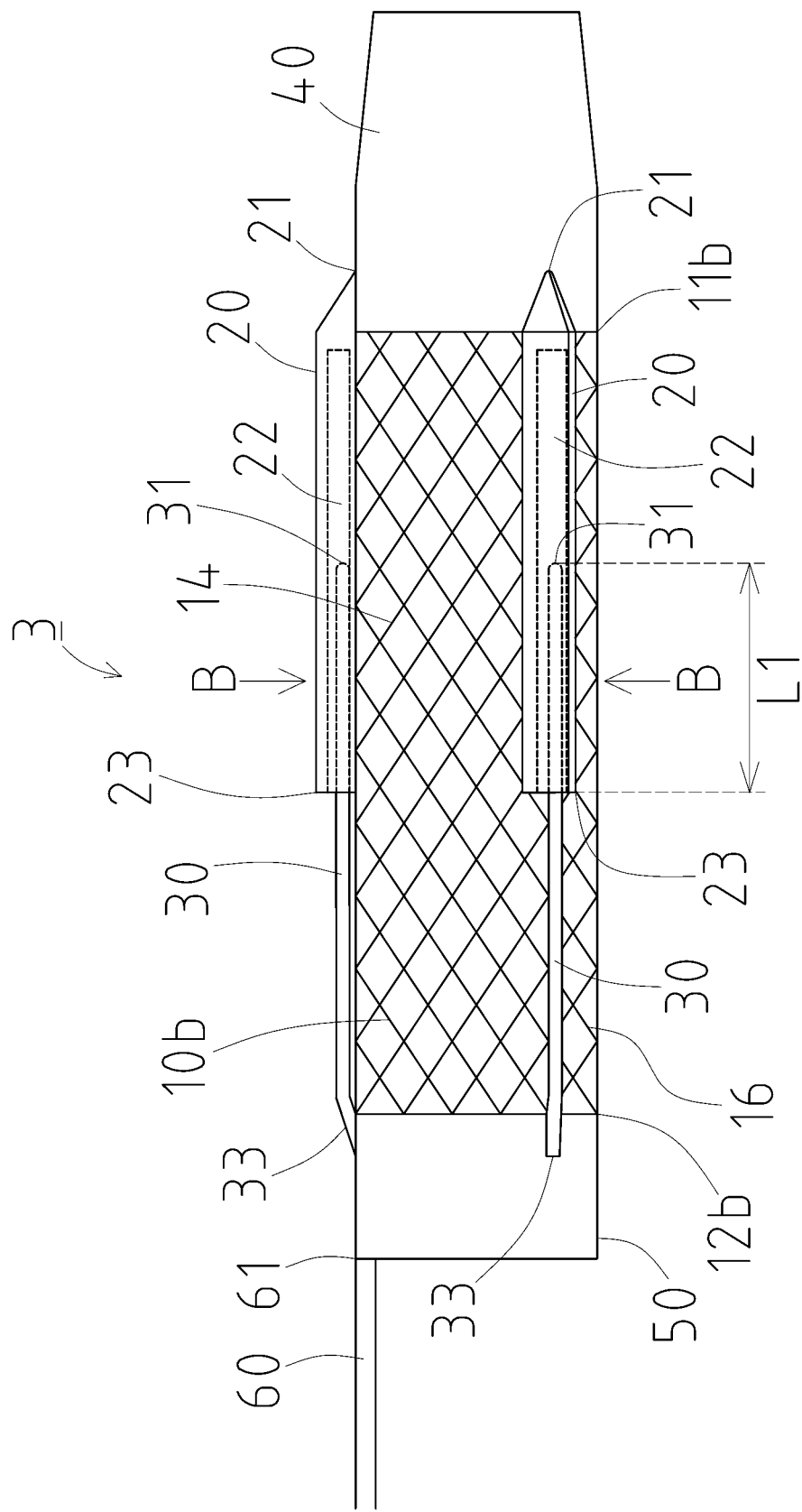
FIG. 6 is an overall view of a medical device according to the disclosed embodiments, in which an expandable-and-contractible member is radially contracted.
Figure 7:
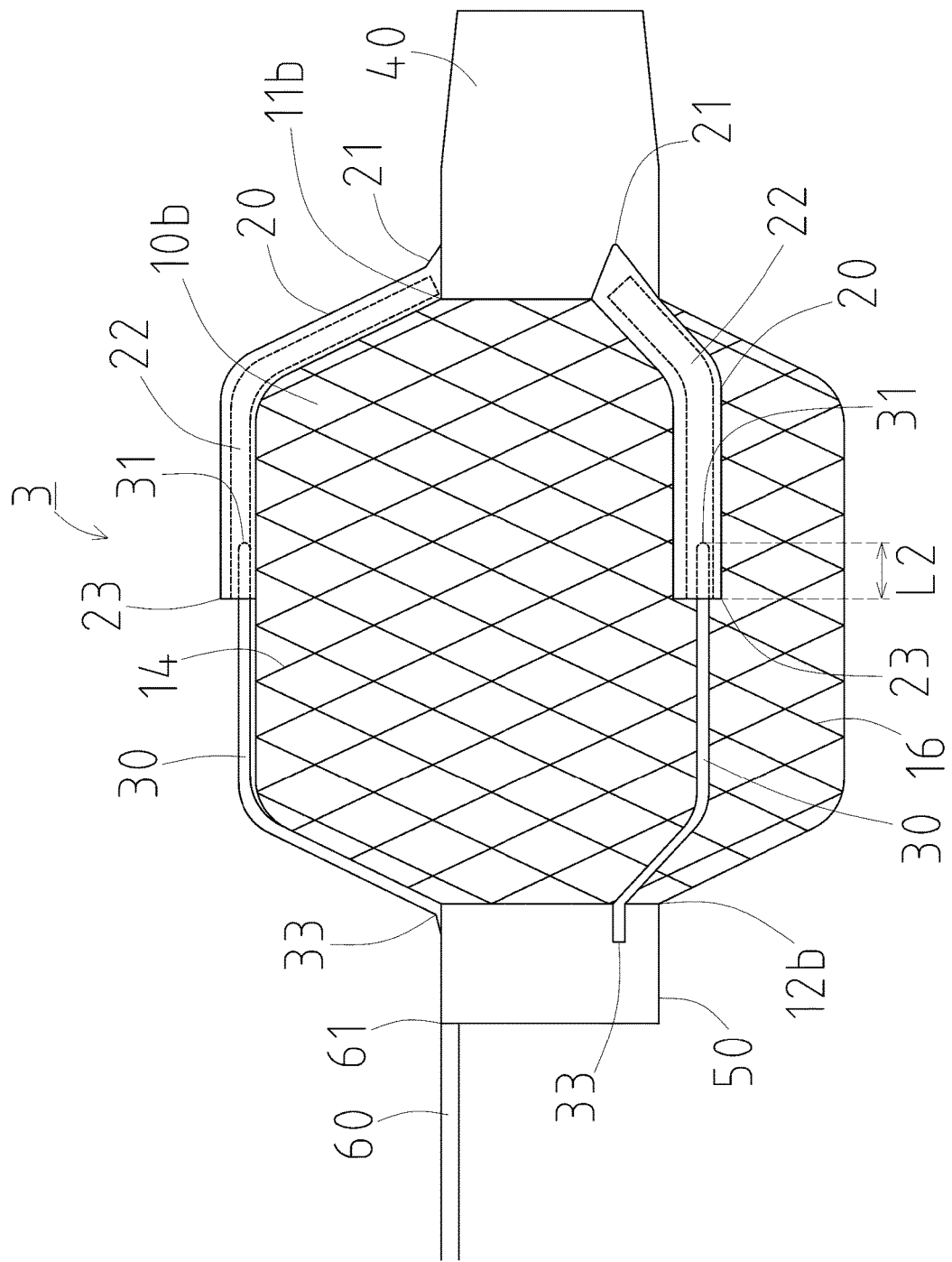
FIG. 7 is an overall view of the medical device shown in FIG. 6, in which the expandable-and-contractible member is radially expanded.

Next, a medical device 3 according to the disclosed embodiments is described below referring to FIG. 6 to FIG. 8. FIG. 6 shows an expandable-and-contractible member 10b radially contracted, and FIG. 7 shows the expandable-and-contractible member 10b radially expanded. Description of the medical device 3 below only includes its differences from the medical device 1.

The medical device 3 is similar to the medical device 1 except that it comprises the expandable-and-contractible member 10b instead of the expandable-and-contractible member 10. The expandable-and-contractible member 10b is a mesh member having a mesh configuration (a net configuration) woven from a first wire 14 and a second wire 16 (see FIG. 6 and FIG. 7). A distal end 11b of the expandable-and-contractible member 10b is fixed to the distal tip 40, and a proximal end 12b of the expandable-and-contractible member 10b is fixed to the ring 50.

Figure 8:
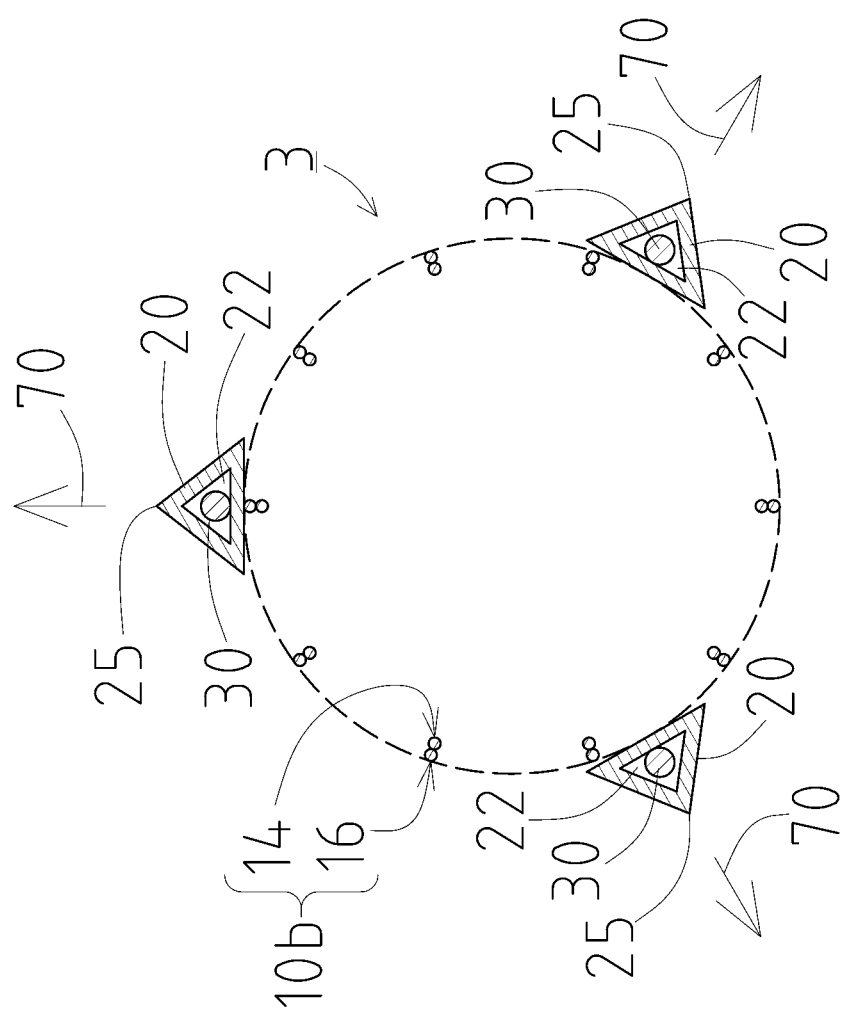
FIG. 8 is a sectional view taken from line B-B of FIG. 6.

FIG. 8 is a sectional view taken from line B-B of FIG. 6. On an outer circumference of the expandable-and-contractible member 10b of the medical device 3, similarly to the case of the medical device 1, three incising members 20 are disposed in an arrangement in which they are spaced from each other by 120 degrees in the circumferential direction. As discussed above with reference to the medical device 1, the incising member 20 is a triangular tube with its interior being the hollow portion 22, and comprises the protruding portion 25 protruding outwardly. Upon radial expansion of the expandable-and-contractible member 10b, the incising member 20 moves in the direction shown by the arrow 70 (see FIG. 3), so that the protruding portion 25 of the incising member 20 can incise a stenosis or stricture.

In the medical device 3, the core wire 30, which is inserted in the hollow portion 22 of the incising member 20 from the proximal end of the medical device 3, can slide in the longitudinal direction within the hollow portion 22 as the expandable-and-contractible member 10b expands or contracts. More specifically, upon radial expansion of the expandable-and-contractible member 10b (in other words, upon transitioning from the state shown in FIG. 6 to the state shown in FIG. 7), part of the core wire 30 housed within the hollow portion 22 of the incising member 20 becomes shorter in the longitudinal direction from L1 to L2, while, upon radial contraction of the expandable-and-contractible member 10b (in other words, upon transitioning from the state shown in FIG. 7 to the state shown in FIG. 6), the part of the core wire 30 housed within the hollow portion 22 of the incising member 20 becomes longer in the longitudinal direction from L2 to L1.

As described above, in the medical device 3, the incising member 20 is not fixed to the expandable-and-contractible member 10b, and, because the core wire 30 is inserted in the hollow portion 22, the incising member 20 does not come off the expandable-and-contractible member 10b as the expandable-and-contractible member 10b expands or contracts and can slide to an optimum position, consequently reducing the possibility of the incising member 20 interfering with the radial expansion or the radial contraction of the expandable-and-contractible member 10b. Even when the stenosis or stricture is partially caught between the expandable-and-contractible member 10b and the incising member 20 and the handler manipulates the medical device 1 in the longitudinal direction in that state, the core wire 30 can be pulled out of the hollow portion 22 of the incising member 20 (in other words, the core wire 30 and the incising member 20 can become separated from each other), so that the load (external force) applied on the incising member 20 by the stenosis or stricture thus caught can be reduced, consequently reducing the possibility of the incising member 20 coming off the expandable-and-contractible member 10b.

Figure 9:
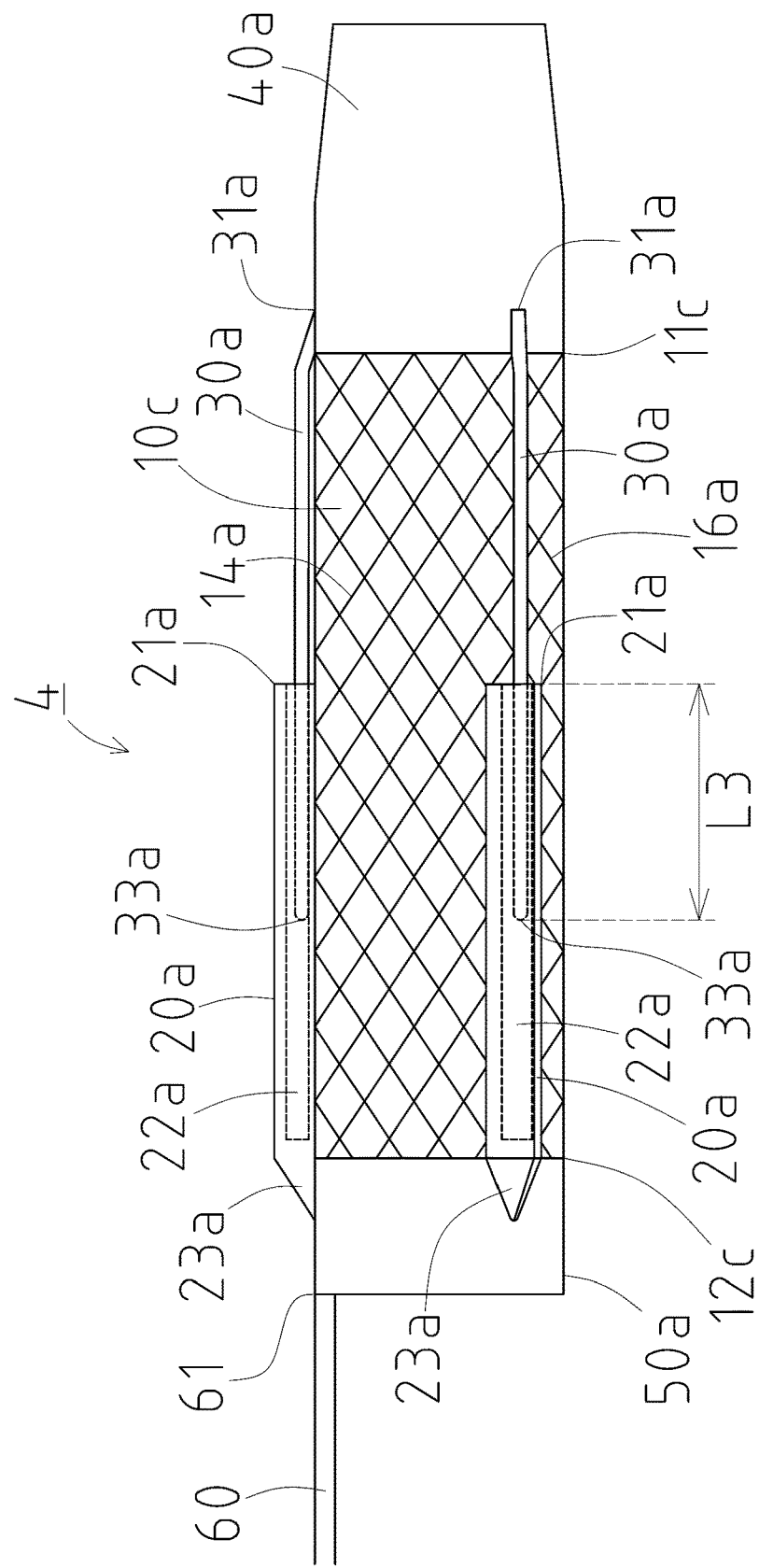
FIG. 9 is an overall view of a medical device according to the disclosed embodiments, in which an expandable-and-contractible member is radially contracted.
Figure 10:
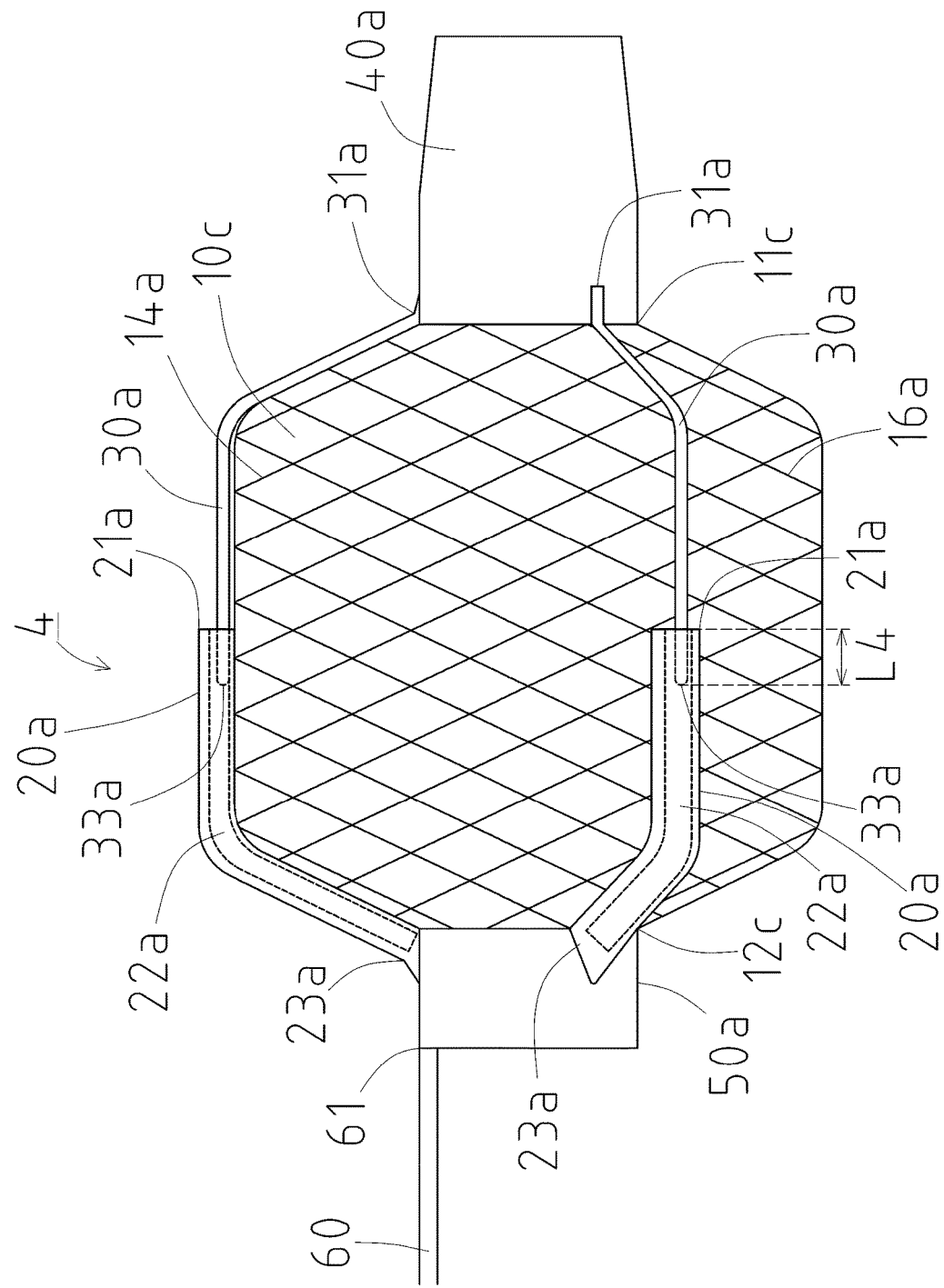
FIG. 10 is an overall view of the medical device shown in FIG. 9, in which the expandable-and-contractible member is radially expanded.

Next, a medical device 4 according to the disclosed embodiments is described below referring to FIG. 9 and FIG. 10. FIG. 9 shows an expandable-and-contractible member 10c radially contracted, and FIG. 10 shows the expandable-and-contractible member 10c radially expanded. Description of the medical device 4 below only includes its differences from the medical device 2.

The medical device 4 comprises the expandable-and-contractible member 10c, instead of the expandable-and-contractible member 10a. The expandable-and-contractible member 10c is a mesh member having a mesh configuration (a net configuration) woven from a first wire 14a and a second wire 16a (see FIG. 9 and FIG. 10). A distal end 11c of the expandable-and-contractible member 10c is fixed to the distal tip 40a, and a proximal end 12c of the expandable-and-contractible member 10c is fixed to the ring 50a.

In the medical device 4, the core wire 30a, which is inserted in the hollow portion 22a of the incising member 20a from the distal end of the medical device 4, can slide in the longitudinal direction within the hollow portion 22a as the expandable-and-contractible member 10c expands or contracts. More specifically, upon radial expansion of the expandable-and-contractible member 10c (in other words, upon transitioning from the state shown in FIG. 9 to the state shown in FIG. 10), part of the core wire 30a housed within the hollow portion 22a of the incising member 20a becomes shorter in the longitudinal direction from L3 to L4, while, upon radial contraction of the expandable-and-contractible member 10c (in other words, upon transitioning from the state shown in FIG. 10 to the state shown in FIG. 9), the part of the core wire 30a housed within the hollow portion 22a of the incising member 20a becomes longer in the longitudinal direction from L4 to L3.

As described above, in the medical device 4, the incising member 20a is not fixed to the expandable-and-contractible member 10c, and, because the core wire 30a is inserted in the hollow portion 22a, the incising member 20a does not come off the expandable-and-contractible member 10c as the expandable-and-contractible member 10c expands or contracts and can slide to an optimum position, consequently reducing the possibility of the incising member 20a interfering with the radial expansion or the radial contraction of the expandable-and-contractible member 10c. Even when the stenosis or stricture is partially caught between the expandable-and-contractible member 10c and the incising member 20a and the handler manipulates the medical device 4 in the longitudinal direction in that state, the core wire 30a can be pulled out of the hollow portion 22a of the incising member 20a (in other words, the core wire 30a and the incising member 20a can become separated from each other), so that the load (external force) applied on the incising member 20a by the stenosis or stricture thus caught can be reduced, consequently reducing the possibility of the incising member 20a coming off the expandable-and-contractible member 10c.

Figure 11:
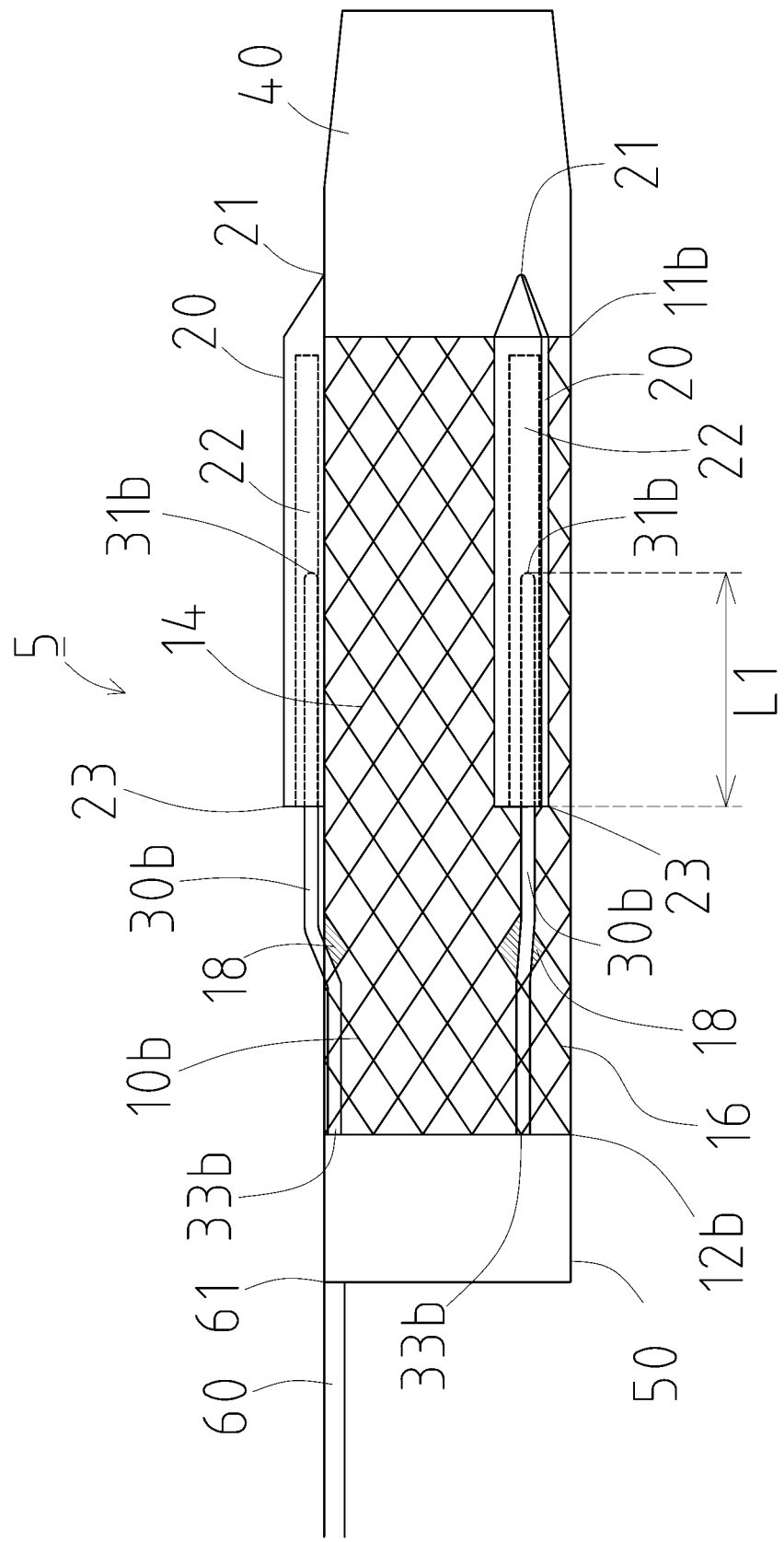
FIG. 11 is an overall view of a medical device according to the disclosed embodiments, in which an expandable-and-contractible member is radially contracted.
Figure 12:
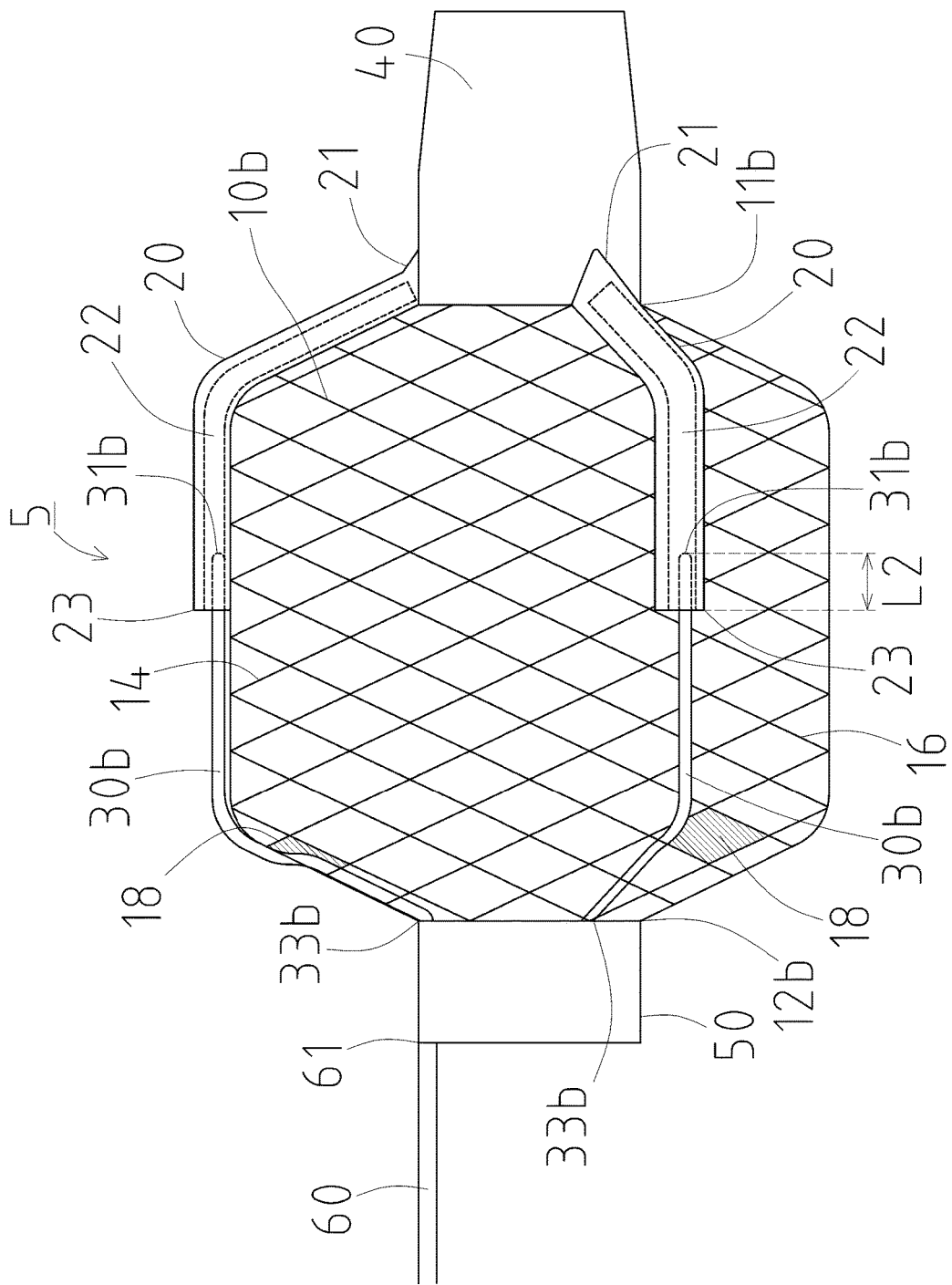
FIG. 12 is an overall view of the medical device shown in FIG. 11, in which the expandable-and-contractible member is radially expanded.

Next, a medical device 5 according to the disclosed embodiments is described below referring to FIG. 11 and FIG. 12. FIG. 11 shows the expandable-and-contractible member 10b radially contracted, and FIG. 12 shows the expandable-and-contractible member 10b radially expanded. Description of the medical device 5 below only includes its differences from the medical device 3.

In the medical device 5, a core wire 30b extends out of the expandable-and-contractible member 10b in the distal direction at one of spaces 18 defined by the first wire 14 and the second wire 16, as seen from a proximal end 33b of the core wire 30b toward a distal end 31b of the core wire 30b. In other words, as seen from the distal end 31b toward the proximal end 33b, the core wire 30b extends in the proximal direction and enters the expandable-and-contractible member 10b through the spaces 18 defined by the first wire 14 and the second wire 16, and then, at the proximal end 33b, it is fixed to the ring 50.

Similarly to the case of the medical device 3, the core wire 30b, which is inserted in the hollow portion 22 of the incising member 20 from the proximal end of the medical device 5, can slide in the longitudinal direction within the hollow portion 22 as the expandable-and-contractible member 10b expands or contracts. More specifically, upon radial expansion of the expandable-and-contractible member 10b (in other words, upon transitioning from the state shown in FIG. 11 to the state shown in FIG. 12), part of the core wire 30b housed within the hollow portion 22 of the incising member 20 becomes shorter in the longitudinal direction from L1 to L2, while, upon radial contraction of the expandable-and-contractible member 10b (in other words, upon transitioning from the state shown in FIG. 12 to the state shown in FIG. 11), the part of the core wire 30b housed within the hollow portion 22 of the incising member 20 becomes longer in the longitudinal direction from L2 to L1.

In the medical device 5, in which only a short part of the core wire 30b sticks out of the expandable-and-contractible member 10b from one of the spaces 18, even if the core wire 30b is pulled out of the hollow portion 22 of the incising member 20 (in other words, the core wire 30b and the incising member 20 become separated from each other), the likelihood of the core wire 30b moving outwardly and coming off the expandable-and-contractible member 10b is reduced, and, as a result, the possibility of a wall of a normal blood vessel or a wall of a normal digestive organ becoming impaired by the core wire 30b being pulled out of (or separated from) the incising member 20 can be reduced.

Figure 13:
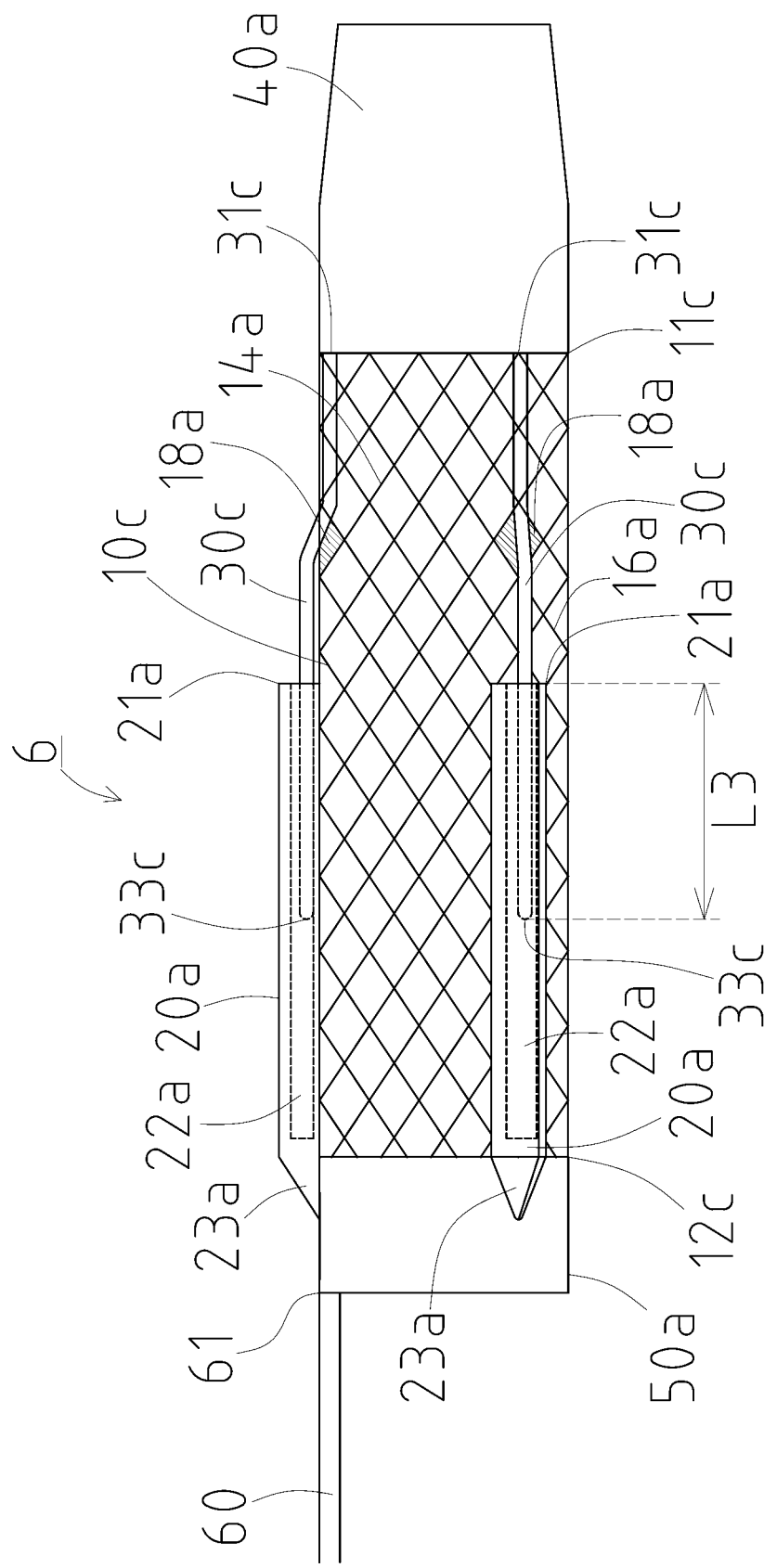
FIG. 13 is an overall view of a medical device according to the disclosed embodiments, in which an expandable-and-contractible member is radially contracted.
Figure 14:
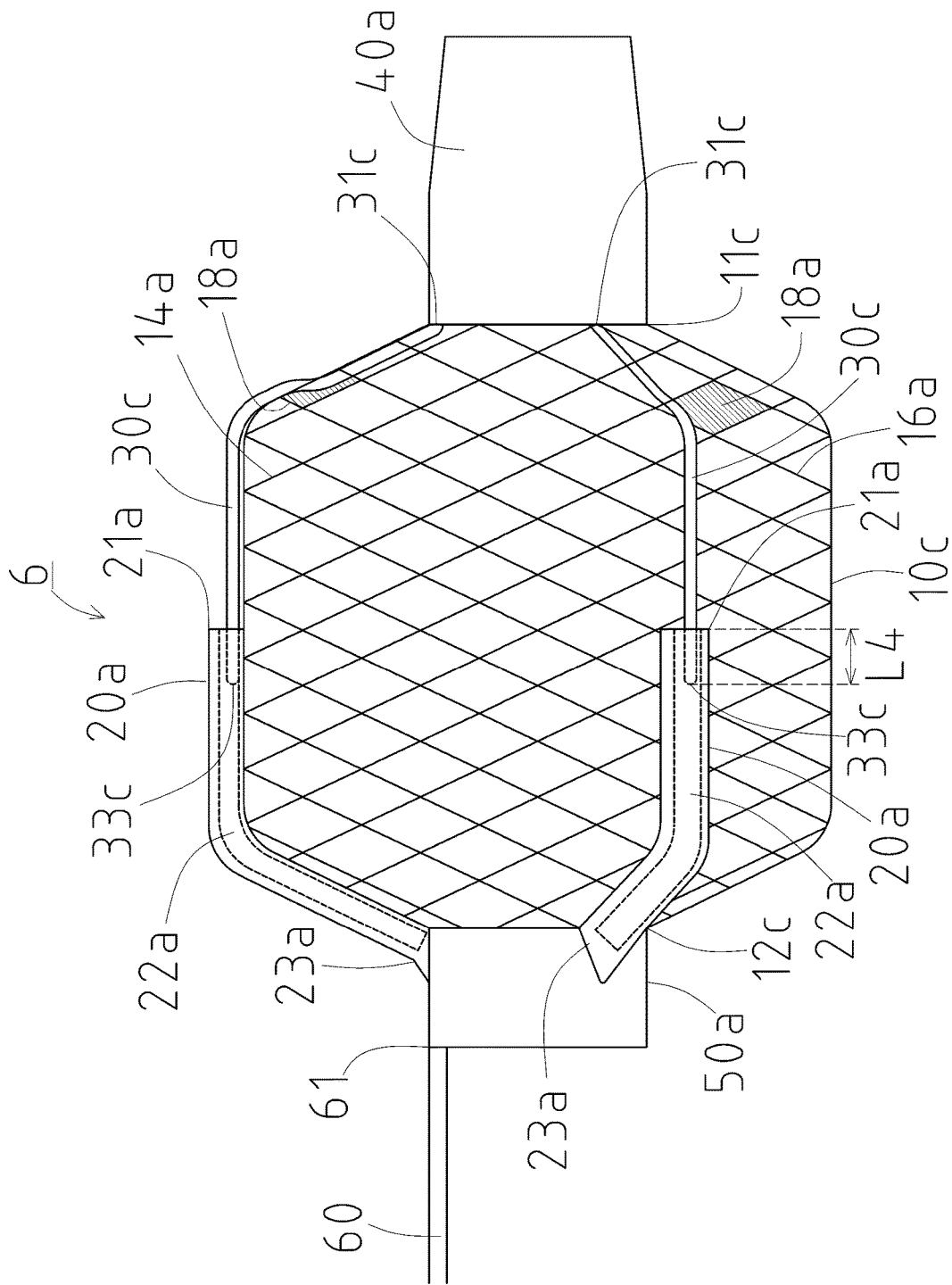
FIG. 14 is an overall view of the medical device shown in FIG. 13, in which the expandable-and-contractible member is radially expanded.

Next, a medical device 6 according to the disclosed embodiments is described below referring to FIG. 13 and FIG. 14. FIG. 13 shows the expandable-and-contractible member 10c radially contracted, and FIG. 14 shows the expandable-and-contractible member 10c radially expanded. Description of the medical device 6 below only includes its differences from the medical device 4.

In the medical device 6, a core wire 30c extends out of the expandable-and-contractible member 10c in the proximal direction at one of spaces 18a defined by the first wire 14a and the second wire 16a, as seen from a distal end 31c of the core wire 30c toward a proximal end 33c of the core wire 30c. In other words, as seen from the proximal end 33c toward the distal end 31c, the core wire 30c extends in the distal end direction and enters the expandable-and-contractible member 10c through the spaces 18a defined by the first wire 14a and the second wire 16a, and then, at the distal end 31c, it is fixed to the distal tip 40a.

Similarly to the case of the medical device 4, the core wire 30c, which is inserted in the hollow portion 22a of the incising member 20a from the distal end of the medical device 6, can slide in the longitudinal direction within the hollow portion 22a as the expandable-and-contractible member 10c expands or contracts. More specifically, upon radial expansion of the expandable-and-contractible member 10c (in other words, upon transitioning from the state shown in FIG. 13 to the state shown in FIG. 14), part of the core wire 30c housed within the hollow portion 22a of the incising member 20a becomes shorter in the longitudinal direction from L3 to L4, while, upon radial contraction of the expandable-and-contractible member 10c (in other words, upon transitioning from the state shown in FIG. 14 to the state shown in FIG. 13), the part of the core wire 30c housed within the hollow portion 22a of the incising member 20a becomes longer in the longitudinal direction from L4 to L3.

In the medical device 6, in which only a short part of the core wire 30c sticks out of the expandable-and-contractible member 10c from one of the spaces 18a, even if the core wire 30c is pulled out of the hollow portion 22a of the incising member 20a (in other words, the core wire 30c and the incising member 20a become separated from each other), the likelihood of the core wire 30c moving outwardly and coming off the expandable-and-contractible member 10c is reduced, and, as a result, the possibility of the wall of a normal blood vessel or the wall of a normal digestive organ becoming impaired by the core wire 30c being pulled out of (or separated from) the incising member 20a can be reduced.

Figure 15:
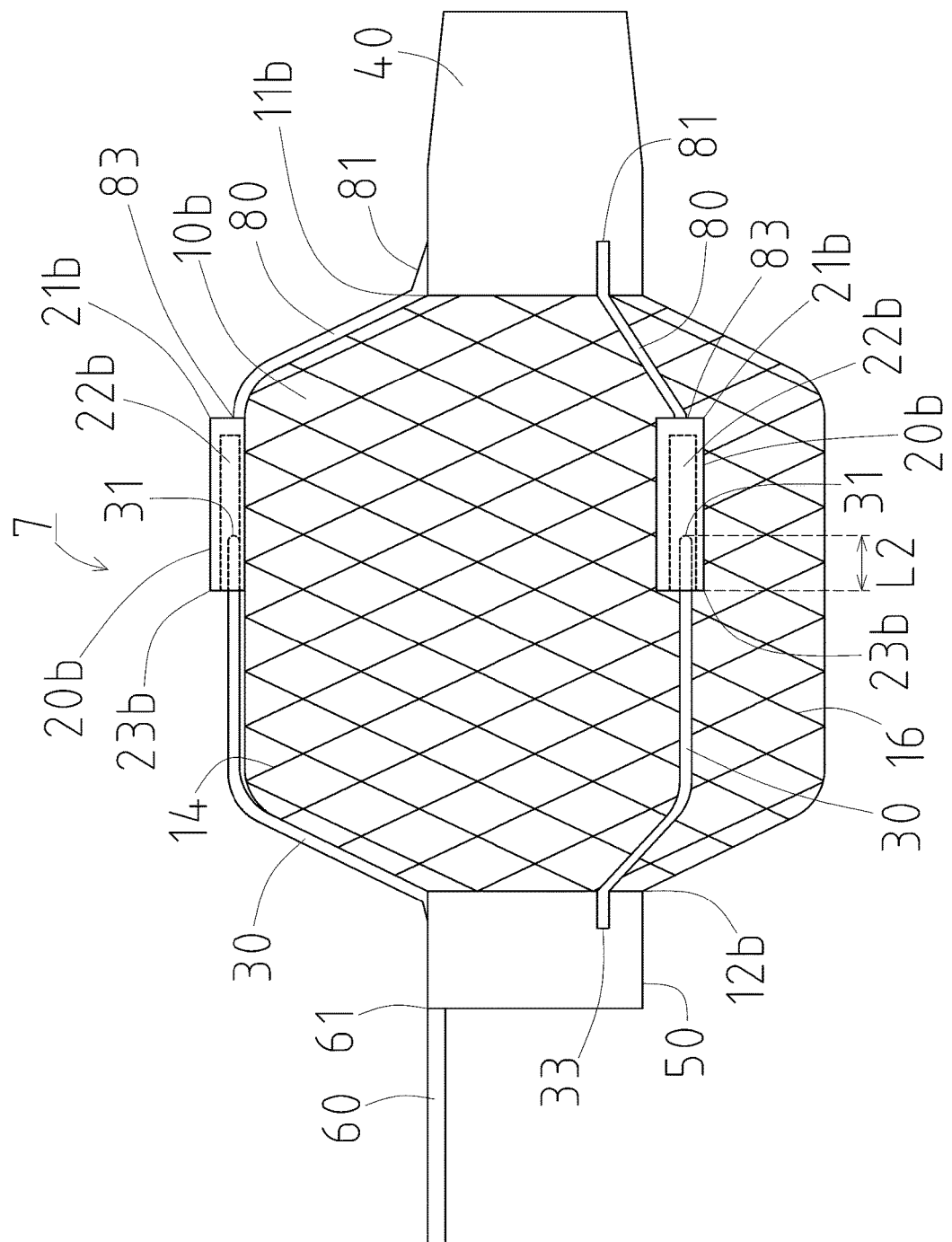
FIG. 15 is an overall view of a medical device according to the disclosed embodiments, in which an expandable-and-contractible member is radially expanded.

In the description of the medical devices 1, 3, and 5, the distal end 21 of the incising member 20 is directly fixed to the distal tip 40, but the medical device is not limited to this configuration. For example, as a variation of the medical device 3 in FIG. 7, a medical device 7 may have a configuration shown in FIG. 15. In FIG. 15, a connecting member 80 is provided between a distal end 21b of an incising member 20b and the distal tip 40. More specifically, the distal end 21b of the incising member 20b is fixed to a proximal end 83 of the connecting member 80, and a distal end 81 of the connecting member 80 is fixed to the distal tip 40. The proximal end 23b of the incising member 20b is not fixed to the expandable-and-contractible member 10b and remains unconstrained.

In the medical device 7, similarly to the case in the medical device 3, the core wire 30 inserted in a hollow portion 22b of the incising member 20b from the proximal end of the medical device 7 can slide in the longitudinal direction within the hollow portion 22b as the expandable-and-contractible member 10b expands or contracts.

In the medical devices 2, 4, and 6, the proximal end 23a of the incising member 20a is directly fixed to the ring 50a, but the medical device is also not limited to this configuration. Alternatively, a connecting member 80 (not shown) may be provided between the incising member 20a and the ring 50a.

Figure 16:
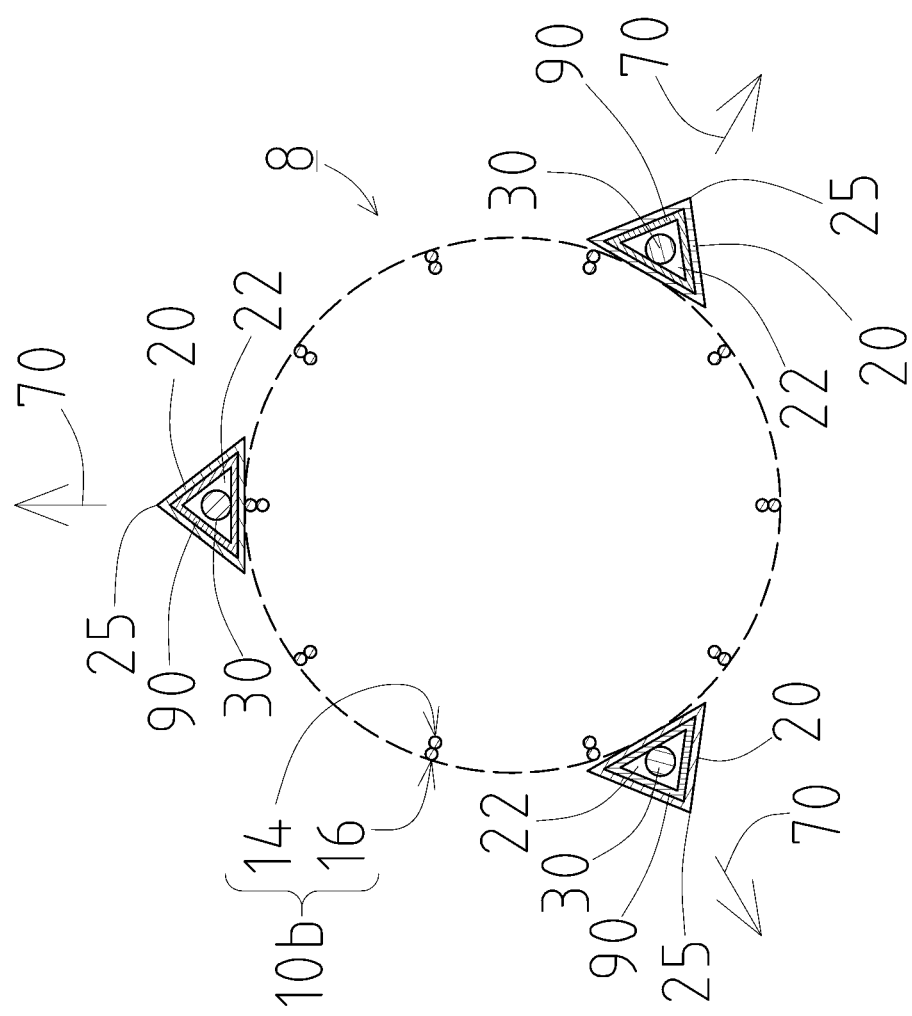
FIG. 16 is a sectional view of a medical device according to the disclosed embodiments.

In the descriptions of the medical devices 1 to 7, the incising member 20, 20a, or 20b is made of monolayer material, but the medical device is not limited to this configuration. For example, as a variation of the medical device 3 shown in FIG. 8, FIG. 16 shows a medical device 8. In FIG. 16, an inner surface of the incising member 20 is covered with a resin layer 90 with low sliding resistance (polytetrafluoroethylene (PTFE) or polyimide, for example) so that the core wire 30 inserted in the hollow portion 22 of the incising member 20 can easily slide in the longitudinal direction as the expandable-and-contractible member 10b expands or contracts.

The expandable-and-contractible member 10 or 10a may be made of polyamide, or another resin material such as polyester, polyurethane, polyolefin, polytetrafluoroethylene, or a silicone resin, for example.

The first wire 14 and the second wire 16 may be made of a Co—Cr alloy with high tensile strength, or another metal material such as stainless steel, W, Pt, a Pt—Ni alloy, an Ni—Ti alloy, or a Cu—Al—Ni alloy. The material of the first wire 14 may be different from the material of the second wire 16. Preferably, at least one of the first wire 14 and the second wire 16 is made of a radiopaque material (tungsten, for example) because, in that case, the handler can use imaging to see exactly where the expandable-and-contractible member 10b or 10c is and consequently can easily place the expandable-and-contractible member 10b or 10c in the site of a stenosis or stricture.

In the medical devices 1 to 8, the incising member 20, 20a, or 20b and the core wire 30, 30a, 30b, or 30c may be made of stainless steel or another metal material such as W, Pt, a Pt—Ni alloy, an Ni—Ti alloy, or a Cu—Al—Ni alloy, or may be made of a hard resin material such as polyimide or polyether ether ketone (PEEK).

The number of the incising member 20, 20a, or 20b and the number of the core wire 30, 30a, 30b, or 30c are not limited to three. At least one incising member 20, 20a, or 20b and at least one core wire 30, 30a, 30b, or 30c are simply required to be disposed on the outer circumference of the expandable-and-contractible member 10, 10a, 10b, or 10c.

What is claimed is:

1. A medical device comprising:
    an expandable-and-contractible member capable of radially expanding and radially contracting;
    an incising member disposed on an outer circumference of the expandable-and-contractible member and comprising a hollow portion open toward a proximal end of the medical device;
    a core wire inserted in the hollow portion of the incising member from the proximal end of the medical device;
    a distal tip fixed to a distal end of the expandable-and-contractible member; and
    a ring fixed to both a proximal end of the expandable-and-contractible member and a proximal end of the core wire,
    wherein:
    a distal end of the incising member is fixed to the distal tip, and a proximal end of the incising member is not fixed to the expandable-and-contractible member and remains unconstrained, and
    the core wire is capable of sliding in a longitudinal direction of the medical device within the hollow portion as the expandable-and-contractible member expands or contracts.

2. The medical device according to claim 1, wherein the expandable-and-contractible member is a mesh member woven from a first wire and a second wire.

3. The medical device according to claim 2, wherein the core wire extends, in a direction toward a distal end of the medical device, from inside the expandable-and-contractible member to outside the expandable-and-contractible member through a space that is defined by the first wire and the second wire.

4. The medical device according to claim 3, wherein an inner surface of the incising member is covered with a resin layer.

5. The medical device according to claim 4, wherein the resin layer is formed of polytetrafluoroethylene (PTFE).

6. The medical device according to claim 2, wherein the incising member is a triangular tube with its interior being the hollow portion.

7. The medical device according to claim 6, wherein an inner surface of the hollow portion is covered with polytetrafluoroethylene (PTFE).

8. The medical device according to claim 1, wherein the incising member is a triangular tube with its interior being the hollow portion.

9. The medical device according to claim 8, wherein an inner surface of the hollow portion is covered with polytetrafluoroethylene (PTFE).

10. A medical device comprising:
    an expandable-and-contractible member capable of radially expanding and radially contracting;
    an incising member disposed on an outer circumference of the expandable-and-contractible member and comprising a hollow portion open toward a proximal end of the medical device;
    a core wire inserted in the hollow portion of the incising member from the proximal end of the medical device;
    a distal tip fixed to both a distal end of the expandable-and-contractible member and a distal end of the incising member; and
    a ring fixed to both a proximal end of the expandable-and-contractible member and a proximal end of the core wire,
    wherein:
    the expandable-and-contractible member is a mesh member woven from a first wire and a second wire, and
    the core wire extends, in a direction toward a distal end of the medical device, from inside the expandable-and-contractible member to outside the expandable-and-contractible member through a space that is defined by the first wire and the second wire, and is capable of sliding in a longitudinal direction of the medical device within the hollow portion as the expandable-and-contractible member expands or contracts.

* * * * *